(12) United States Patent
DeSmet et al.

(10) Patent No.: US 7,604,667 B2
(45) Date of Patent: Oct. 20, 2009

(54) UNITARY ACETABULAR CUP PROSTHESIS WITH EXTENSION FOR DEFICIENT ACETABULUM

(75) Inventors: Koen DeSmet, Heusden (BE); Steven F. Seyer, Shelton, CT (US); Anthony J. Svarczkopf, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 11/574,907

(22) PCT Filed: Sep. 13, 2005

(86) PCT No.: PCT/US2005/032788

§ 371 (c)(1),
(2), (4) Date: Mar. 21, 2008

(87) PCT Pub. No.: WO2006/031911

PCT Pub. Date: Mar. 23, 2006

(65) Prior Publication Data

US 2008/0262627 A1  Oct. 23, 2008

(51) Int. Cl.
*A61F 2/32*  (2006.01)
(52) U.S. Cl. .................... 623/22.36; 623/22.21
(58) Field of Classification Search .... 623/22.21–22.39
See application file for complete search history.

(56) References Cited

U.S. PATENT DOCUMENTS

| | | | | | |
|---|---|---|---|---|---|
| 3,903,549 | A | * | 9/1975 | Deyerle ................... | 623/22.36 |
| 4,298,993 | A | * | 11/1981 | Kovaleva et al. ......... | 623/22.36 |
| 4,623,351 | A | * | 11/1986 | Church .................... | 623/22.25 |
| 4,961,748 | A | * | 10/1990 | Frey et al. ................ | 623/22.21 |
| 5,108,447 | A | * | 4/1992 | Zeiler et al. .............. | 623/22.14 |
| 5,176,711 | A | * | 1/1993 | Grimes ................... | 623/22.22 |
| 5,192,329 | A | * | 3/1993 | Christie et al. ........... | 623/22.22 |
| 5,314,488 | A | * | 5/1994 | Hayashi et al. .......... | 623/22.36 |
| 5,314,490 | A | * | 5/1994 | Wagner et al. ........... | 623/22.36 |
| 5,326,368 | A | * | 7/1994 | Collazo ................... | 623/22.22 |
| 5,370,703 | A | * | 12/1994 | Willert et al. ............ | 623/22.22 |
| 5,425,778 | A | * | 6/1995 | Zichner et al. ........... | 623/22.29 |
| 5,571,201 | A | * | 11/1996 | Averill et al. ............ | 623/22.22 |
| 5,702,477 | A | * | 12/1997 | Capello et al. ........... | 623/22.21 |
| 5,871,548 | A | * | 2/1999 | Sanders et al. ........... | 623/22.36 |
| 5,928,288 | A | * | 7/1999 | Wilson .................... | 623/22.22 |
| 5,931,870 | A | * | 8/1999 | Cuckler et al. ........... | 623/22.21 |
| 6,004,353 | A | * | 12/1999 | Masini .................... | 623/22.21 |
| 6,416,553 | B1 | * | 7/2002 | White et al. ............. | 623/22.38 |
| 6,537,321 | B1 | | 3/2003 | Horber .................... | 623/22.22 |
| 6,620,200 | B1 | * | 9/2003 | Descamps et al. ........ | 623/22.32 |

(Continued)

*Primary Examiner*—Alvin J Stewart

(57) ABSTRACT

A prosthesis for a deficient acetabulum of a patient having a cup portion and a flange member. The flange member has a base portion that extends upward along a portion of the upper rim. A generally planar screw retaining portion extends from the base portion, and is inclined from the base portion such that at least a lateral portion of a lower surface of the screw retaining portion is positioned below the upper rim while an upper surface of the screw retaining portion is positioned above the upper rim. The screw retaining portion has a first threaded hole, a second threaded hole and a neutral threaded hole, with the neutral hole positioned between the first and the second holes. The holes are inclined at certain orientations to allow for fixation with screws in a deficient acetabulum, and for use in a left or right hip.

23 Claims, 15 Drawing Sheets

U.S. PATENT DOCUMENTS

| | | | |
|---|---|---|---|
| 6,840,959 B2 * | 1/2005 | Treacy et al. | 623/22.22 |
| 6,908,486 B2 * | 6/2005 | Lewallen | 623/22.21 |
| 7,485,148 B2 * | 2/2009 | Wozencroft et al. | 623/22.36 |
| 2002/0042654 A1 * | 4/2002 | Masini | 623/22.32 |
| 2003/0171818 A1 * | 9/2003 | Lewallen | 623/22.22 |
| 2005/0004677 A1 * | 1/2005 | Johnson | 623/22.19 |
| 2005/0288793 A1 * | 12/2005 | Dong et al. | 623/22.28 |
| 2006/0052876 A1 * | 3/2006 | Wozencroft et al. | 623/22.32 |
| 2006/0058887 A1 * | 3/2006 | DeSmet et al. | 623/22.36 |
| 2007/0179624 A1 * | 8/2007 | Stone et al. | 623/19.13 |
| 2007/0250175 A1 * | 10/2007 | Meridew et al. | 623/22.21 |
| 2008/0172130 A1 * | 7/2008 | Macara | 623/22.21 |
| 2008/0262627 A1 * | 10/2008 | DeSmet et al. | 623/22.36 |
| 2008/0306606 A1 * | 12/2008 | Shields | 623/22.21 |
| 2009/0088865 A1 * | 4/2009 | Brehm | 623/22.21 |

* cited by examiner

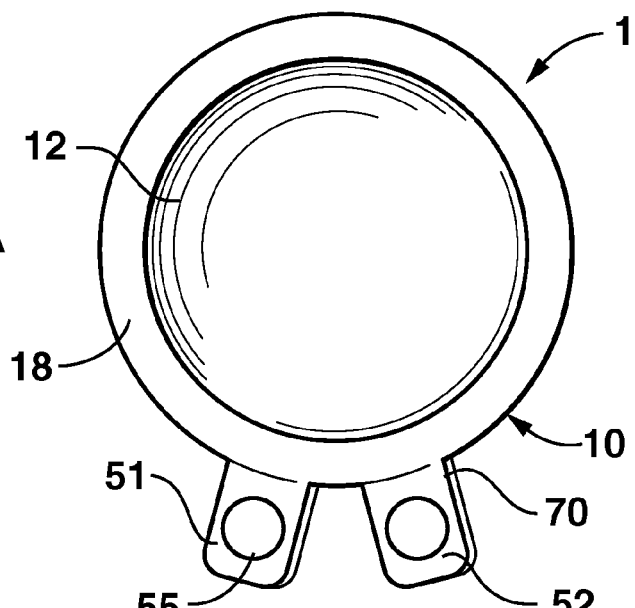
FIG. 2A
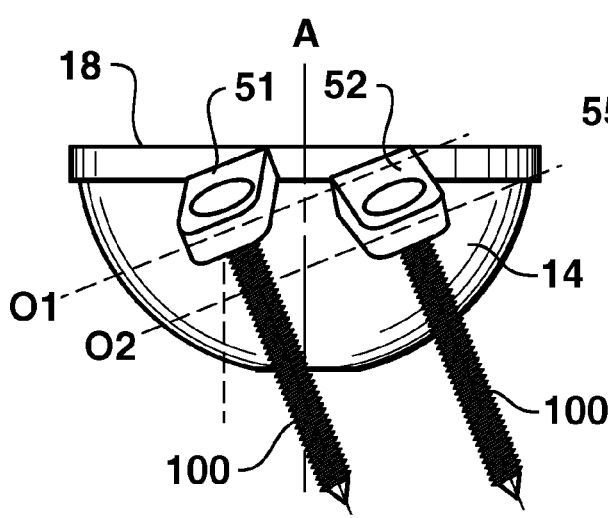
FIG. 2B
FIG. 2C
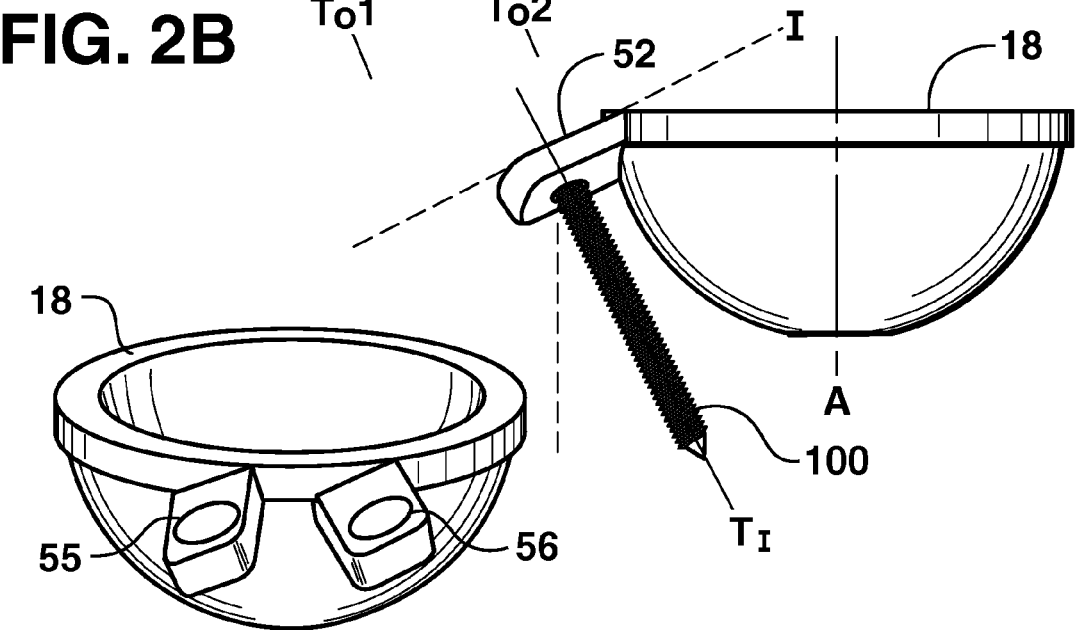
FIG. 2D

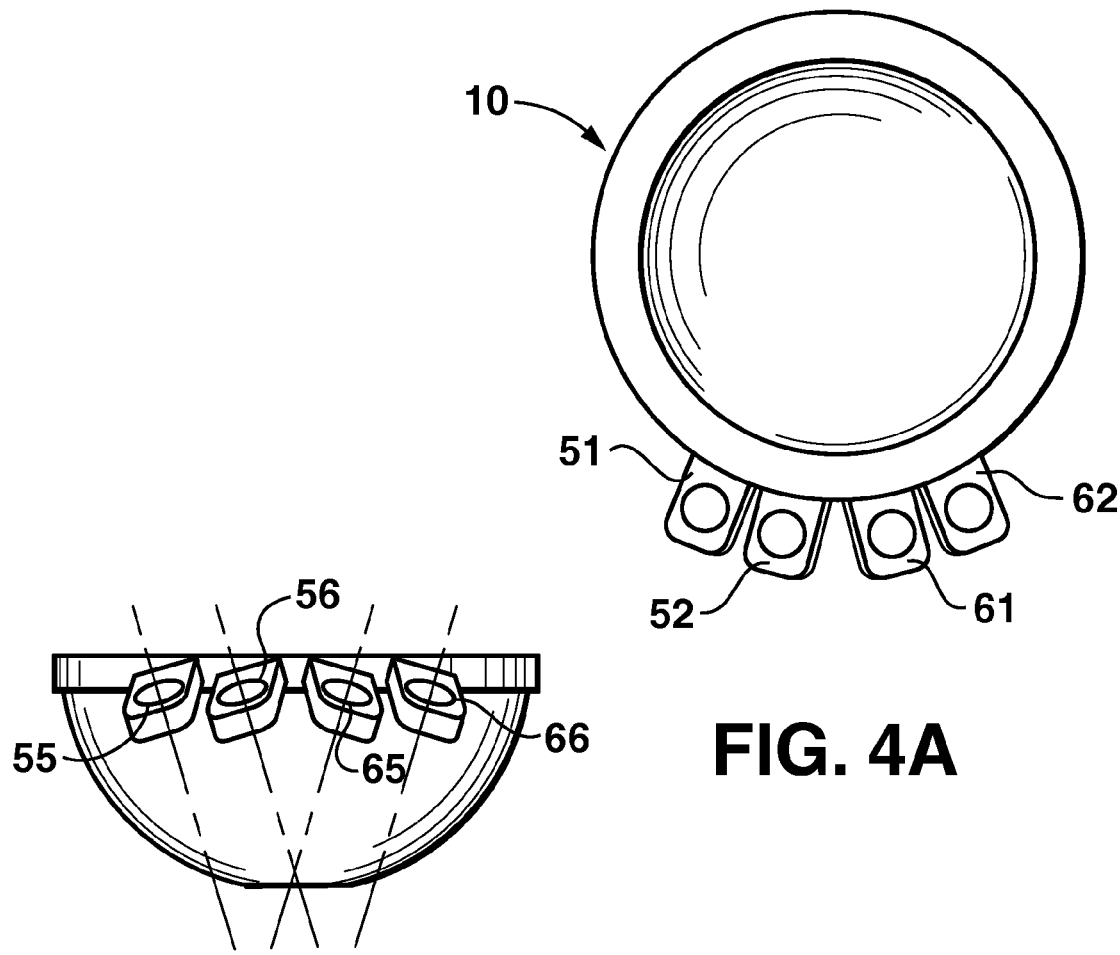
FIG. 4A
FIG. 4B
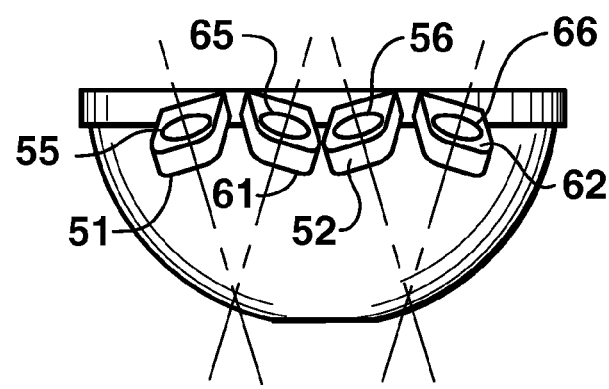
FIG. 4C

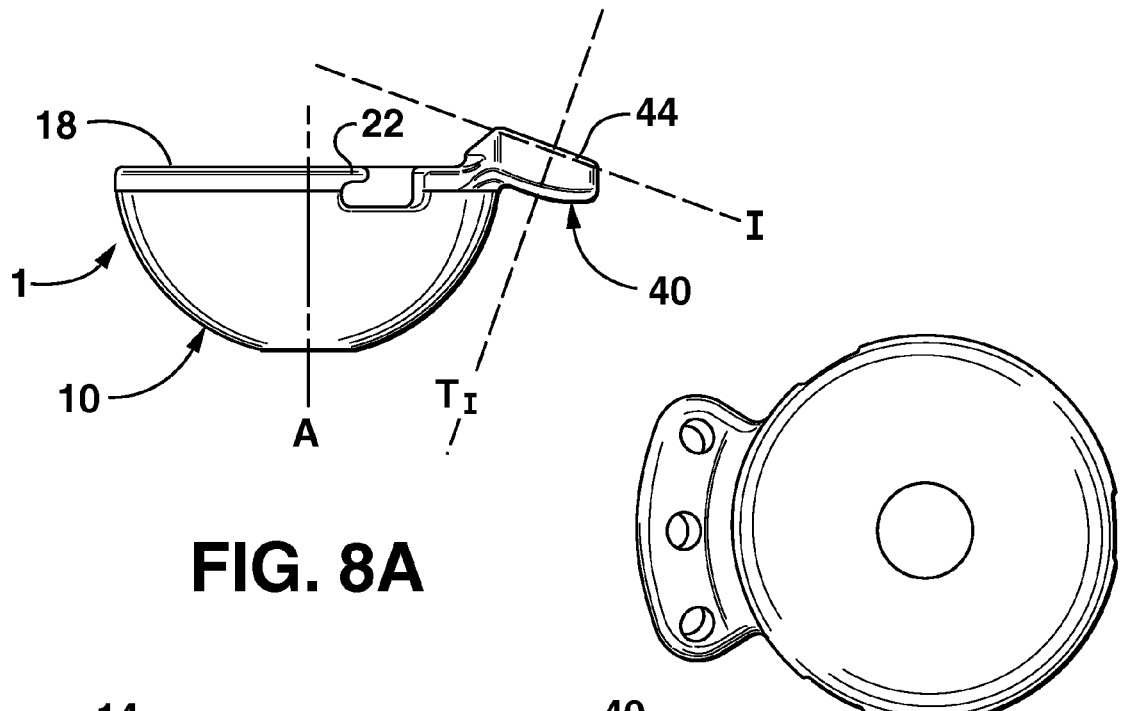
FIG. 8A
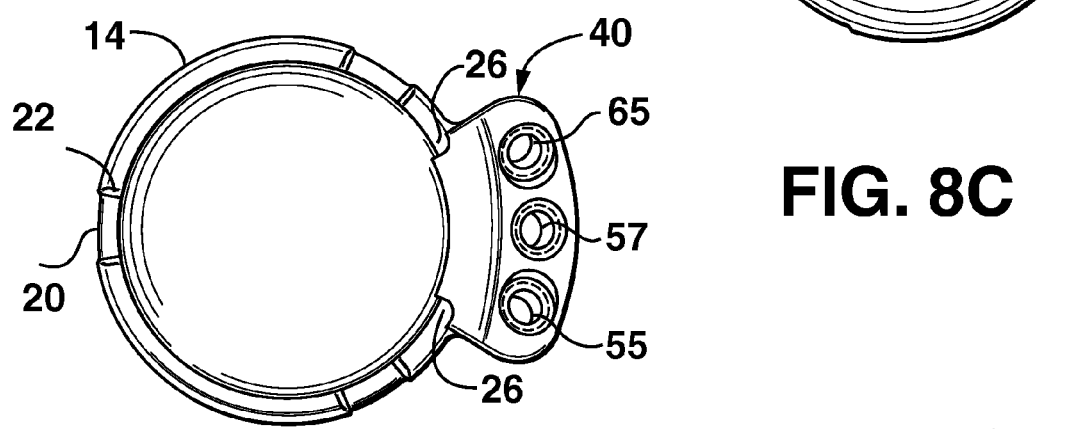
FIG. 8B
FIG. 8C
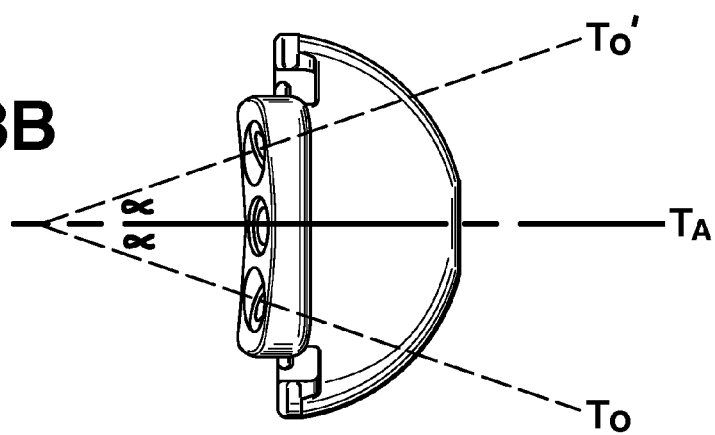
FIG. 8D

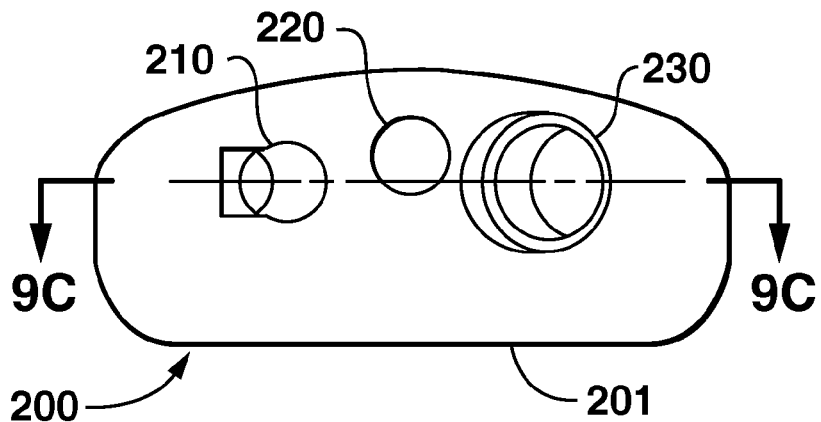
FIG. 9B
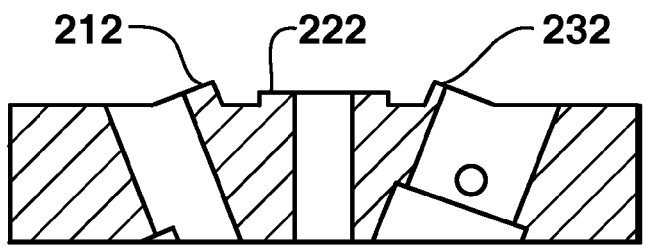
FIG. 9C
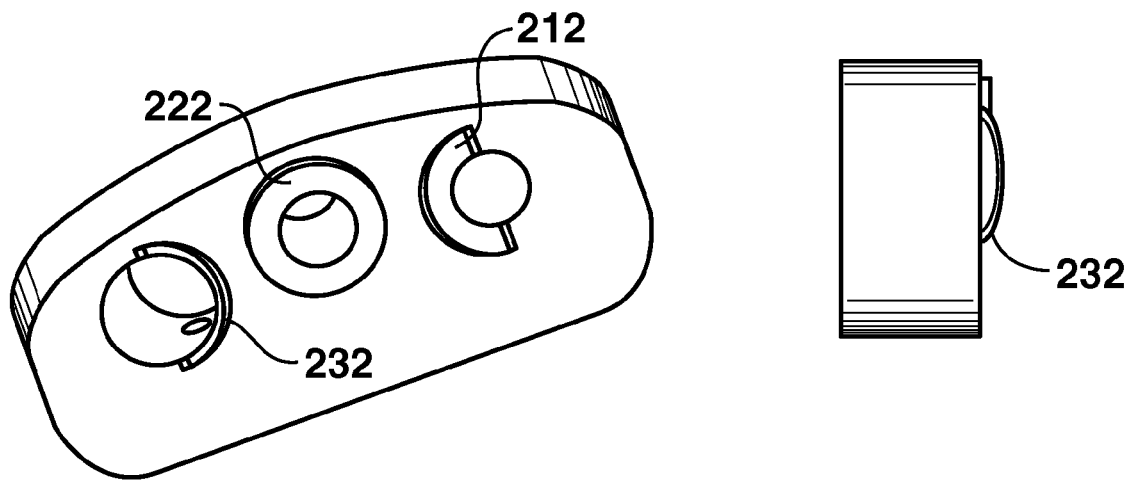
FIG. 9D        FIG. 9E

US 7,604,667 B2

UNITARY ACETABULAR CUP PROSTHESIS WITH EXTENSION FOR DEFICIENT ACETABULUM

CROSS REFERENCE TO RELATED APPLICATIONS

This application claims priority to U.S. patent application Ser. No. 10/941,210 (published as 2006/0058887A1), filed Sep. 15, 2004, which is pending, and to PCT/US/32788 (published as WO 2006/31911), filed Sep. 14, 2005, which is pending.

TECHNICAL FIELD

The present invention relates to orthopedic prosthetic implants, and more particularly to an acetabular cup prosthesis that is configured particularly for treatment of deficient acetabula, such as the type encountered in hip dysplasia or osteoarthritis.

BACKGROUND ART

Conventional acetabular cup prostheses employ a two-part construction comprising a cup portion and a separate bearing insert. The cup is secured in the acetabulum by one or more screws, which pass through the wall of the cup and directly into the bone of the acetabulum. Once the cup is secured, the bearing insert is installed in the cup. To prevent shifting or loosening of the cup, the acetabulum is reamed prior to cup insertion in order to provide a correct fit and a deeper pocket for the cup. To further improve stability, the cup is selected with a diameter large enough to span the widest part of the defect. The cup may also be selected to have a diameter slightly larger than that of the reamed acetabulum, such that a press-fit connection is achieved. However, a larger cup typically requires more reaming than a smaller cup, which may result in removal of viable as well as diseased bone.

Acetabular cup prostheses are used to correct various types of acetabular defects, including defects involving compromised acetabular walls or deficient bone. One type of acetabular defect is congenital hip dysplasia. In congenital hip dysplasia, portions of the rim of the acetabulum may be minimal and the acetabulum is shallower than normal ft is difficult to stabilize a cup prosthesis in a shallow acetabulum because little bone is available for reaming or for threading of screws.

Other deficient acetabular conditions may present problems similar to those encountered with dysplasia. In a revision hip replacement, loosening of the primary prosthesis or removal of bone cement often causes defects in the acetabulum. Infection may cause bone loss that results in a deformed or deficient acetabulum. Following a fracture, an acetabulum may heal in a deformed shape. In each of these situations, it may be desireable to minimize reaming and maximize use of available drillable bone in order to secure the prosthesis.

Conventional prostheses do not provide for secure fixation in deficient hips, such as those encountered in dysplasia, where there is not sufficient bone to allow for proper reaming and threading of screws. An inherent problem of prior art cups is a limited ability to be provided with fixation other than directly through the cup and into the acetabulum. To overcome this problem, attempts have been made to provide cups having an extension portion for use in securing the cup to available bone.

The prior art includes two-part acetabular cup prostheses that include rim extensions for use in securing the cups in deficient acetabula, such as the type encountered in congenital hip dysplasia. See U.S. Pat. No. 5,702,477 (Capello et al.); U.S. Pat. No. 5,931,870 (Cuckler); U.S. Pat. No. 6,162,257 (Gustilo et al.). These devices include screw holes in both the cop portion and the extension portion, such that the cup can he secured directly to the acetabulum and the extension portion can be secured directly to the surrounding bone, thus enhancing prosthesis stability even in deficient bone conditions.

U.S. Pat. No. 4,801,300 (Kurze et al.) recognized limitations in the ability of two-part hip prostheses to treat dysplasia hips. (Column 1, lines 41-42). To overcome this deficiency, Kurze et al. proposed a single-part hip joint socket provided with a perforated flange ring for mooring by implant screws. The flange covers at least two-thirds of the circumference of the hip joint socket. The flange has at least four uniformly distributed bore holes for receiving screws for securing the device on bone. The holes are unthreaded, Kurze et al. is directed primarily toward surface texturing for improving biocompatibility and mechanical stability, Kurze et al. provides no discussion of how the socket would be secured by screws. A disadvantage of Kurze et al. is that it does not provide for angulation of screws into available drillable bone in some deficient bone conditions.

FIG. 1 shows a prior art acetabular cup prostheses that is designed particularly for treatment of a dysplasic acetabulum. As shown in FIGS. 1A and 1B, the prior art cup has a pair of tabs that extend from an outer surface of the cup. Each tab includes a threaded hole for receiving a threaded screw for use in securing the cup in an acetabulum. As shown in FIGS. 1A and 1B, the tabs extend in the same plane as the rim of the cup, and are thus perpendicular to the axis of the cup. As shown in FIGS. 1A and 1B, the axis of each screw hole is parallel to the axis of the cup. One advantage of the acetabular cup of FIG. 1 is that it has a symmetrical configuration, and therefore can be used in either a left or right hip. However, a disadvantage of the acetabular cup of FIG. 1 is that the screws are oriented in a manner that does not maximize use of available drillable bone in some deficient bone conditions, such as those encountered in dysplasia.

The prior art includes a three-hole cup of the type shown in FIG. 10A-10B. The three-hole cup shown in FIG. 10A-10B suffers from several disadvantages. As shown in FIG. 10B, the flange portion extends laterally out from the rim of the cup, such that the top of the flange is even with the rim while the bottom of the flange is below the rim. The flange has a slight incline. The top and bottom of the prior art flange are fiat. The holes of the prior art flange are arranged in a triangular orientation, which results in a long flange. The foregoing features make it difficult to orient the prior art three-hole implant to the contour of the acetabulum. Additionally, the axes of the holes of the prior art flange are oriented parallel to the axis of the cup, which makes it difficult to anchor the implant with sufficient anteversion, particularly in a deficient acetabulum.

GB Patent Application 2,347,864 (Paling) discloses a removeable attachment member that can be used to transform a conventional acetabular cup into a dysplasia cup. A primary objective of Paling is to allow a surgeon to determine intraoperatively whether to use a conventional cup or to convert the cup into a dysplasia cup. To accomplish this objective. Paling discloses an annular portion that is removably mountable on a rim of an acetabular cup and which has one or more integral flanges, each flange having a hole for receiving a screw. In order to negate the resultant moment imparted to the cup through the screws, the annular portion is preferably provided with two diametrically opposed flanges. Additionally, the two flanges are preferably angled relative to the annular portion. The flange angle is at a declination of 20 degrees or substantially 20 degrees from the underside of the annular portion. According to Paling, angulation allows a higher clamping force to be imparted by the ring when acting on the acetabular cup. However, as shown in FIG. 4 of Paling, the axes of the holes remains parallel to the axis of the cup, and thus do not provide for angled threading into bone. Paling discloses mounting the cup portion in the acetabulum in the conventional manner, followed by attachment, of the annular portion to the cup portion such that projections on the annular portion engage recesses in the rim of the cup portion. Screws are then passed through the holes and into bone, such that the annular portion secures the acetabular cup in place. One disadvantage of Paling is that the annular portion is of thin construction, and therefore subject to potential failure. Additionally, because the annular portion is not fixed to the cup portion, there are circumstances in which the annular portion may separate or dislodge from the cup. Further, even in the angulated version of Paling, the screws are not angled so as to maximize use of available drillable bone in some deficient hip conditions.

There is thus a need for a acetabular cup prosthesis having the following characteristics and advantages over the prior art.

OBJECTS AND SUMMARY OF THE INVENTION

It is an object of the invention to provide an acetabular cop prosthesis configured to provide secure implantation in a deficient hip, such as a dyslasic hip.

It is an object of the invention to provide an acetabular cup prosthesis that maximizes the use of available bone in a deficient hip to provide improved stability.

It is an object of the invention to provide an acetabular cup prosthesis that customizes the fit and stability of the cup in deficient acetabulae without requiring excessive reaming of good bone surrounding the deficiency.

It is an object of the invention to reduce inventory by providing a cup prosthesis that can be used in either a right or left acetabulum of a patient.

It is a further object of the invention to provide a universal drill guide that can be used to install the cups of the invention.

The foregoing objects and advantages are obtained by providing a unitary acetabular cup prosthesis for use in a deficient acetabulum of a hip bone of a patient having a cup portion and a pair of adjacent screw retaining members oriented for use in attaching the prosthesis to the patient's hip bone. The cup portion has a generally dome-shaped wall having an axis and an upper rim. An inner bearing surface of the wall is configured to pivotally engage a femoral head of a hip prosthesis. Each screw retaining member extends from an outer surface of the dome substantially along the rim. The screw retaining members are integrally formed with the cup portion such that the screw retaining members are fixedly inclined relative to the rim and fixedly offset relative to the rim. The screw retaining members are oriented in a cooperative relationship with one another to facilitate implantation of the prosthesis in one side of the hip of the patient. Each screw retaining member has a threaded hole therethrough. Each threaded hole is fixedly inclined relative to the rim such that an axis of the threaded hole converges toward the axis of the cup portion in one dimension and such that the axis of the threaded hole is oblique to the axis of the cup portion in a second dimension. To reduce prosthesis inventory, a second pair of screw retaining members may be provided, with the first and second pair of screw retaining members oriented such that the prosthesis can be used in either a left or a right acetabulum of the patient.

In one preferred embodiment, first and second pairs of screw retaining members are formed on a single flange. The flange extends from an outer surface of the dome substantially along a portion of the rim. The flange is integrally formed with the cup portion and is inclined relative to the rim. The first pair of screw retaining members are fixed in a cooperative relationship with, one another to facilitate implantation of the device in a left hip of the patient. The second pair of screw retaining members are fixed in a cooperative relationship with one another to facilitate implantation of the device in a right hip of the patient, bin in an oblique relationship with the first pair of screw retaining members. The first and the second pair of screw retaining members are preferably arranged in a staggered relationship.

In one preferred embodiment, the flange member has a base portion that extends upward along a portion of the upper rim. The base portion serves to raise a portion of the flange member above the rim, which increases the conformity of the implant to the acetabulum of the patient. A generally planar screw retaining portion extends from the base portion. The screw retaining portion is inclined torn the base portion such that at least a lateral portion of a lower surface of the screw retaining portion is positioned below the upper rim while an upper surface of the screw retaining portion is positioned above the upper rim. The screw retaining portion has a first threaded hole, a second threaded hole and a neutral threaded hole formed therethrough. The neutral threaded hole is positioned between the first and the second threaded holes. The first threaded hole, the neutral threaded hole, and the second threaded hole are fixedly inclined relative to the rim such that the axes of the threaded holes incline toward the axis of the cup portion in a first dimension viewed generally along a width-wise side of the flange member. The axes of the first and second threaded hole are also offset laterally from the axis of the cup portion in a second dimension viewed generally along a length-wise side of the flange member. The axis of the neutral threaded bole is substantially parallel to the axis of the cup portion in the second dimension, such that the neutral threaded hole can be used with either the first or the second threaded hole. The first, second and neutral threaded holes are spaced sufficiently adjacent one another to allow the cup prosthesis to be used in either a left or a right hip of a patient.

The implant can be provided in a kit format, such as a surgical kit. In a preferred embodiment, the kit includes a set of differently sized implants and a drill guide. In another preferred embodiment, the kit includes a set of differently sized implants and a set of screws having blended threads.

The foregoing and other objects, features, aspects and advantages of the invention will become more apparent from the following detailed description of the invention when considered in conjunction with the accompanying drawings.

BRIEF DESCRIPTION OF THE DRAWINGS

FIG. 2A is a top view of one preferred embodiment of the acetabular cup prosthesis of the invention.

FIG. 2B is a side view of the cup of FIG. 2A, showing screws having a generally parallel cooperative orientation in an offset dimension.

FIG. 2C is a side perspective view of the cup of FIG. 2B, rotated approximately 90 degrees from FIG. 2B to show inclination of the screw in an inclined dimension.

FIG. 2D is perspective view of the cup of FIGS. 2A-2C.

FIGS. 4A-4C show views of one preferred embodiment of the acetabular cup prosthesis of the invention configured for use in either a left or a right hip of a patient.

FIGS. 8A-8G show views of one preferred embodiment of an acetabular cup prosthesis of the invention having an inclined flange.

FIG. 9A-9E show views of one preferred embodiment of a drill guide for use with an acetabular cup prosthesis of the invention.

PREFERRED EMBODIMENTS OF THE INVENTION

Figure 1A:
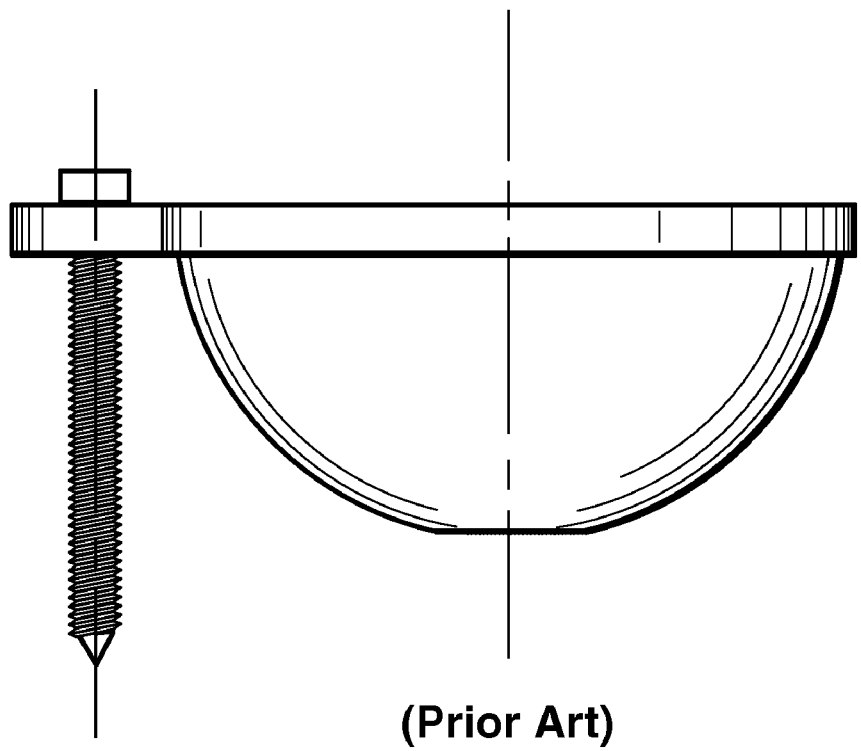
FIG. 1A is a side view of a prior art dysplasia cup, featuring a retaining screw oriented in a parallel relationship with the axis of the cup.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in FIG. 2, the invention is a unitary acetabular cup prosthesis 1 for use in a deficient acetabulum of a hip of a patient. The prosthesis 1 includes a cup portion 10. As shown in FIG. 2B, the cup portion 10 has a generally dome-shaped wall 10 having an axis A and an upper rim 18. As indicated in FIG. 2A, an inner bearing surface 12 of the wall 10 is configured to pivotally engage a femoral head of a femoral hip prosthesis, in a manner known to those of skill in the art. As indicated in FIG. 2B, an outer surface 14 of the dome 10 is sized and configured to reside at least partially within the acetabulum of the patient, in a manner known to those of skill in the art.

As shown in FIG. 2, a pair of first and second screw retaining members 51, 52 are provided for use in attaching the prosthesis to the patient's hip. As shown in FIG. 2B, each screw retaining member extends from the outer surface 14 of the dome 10 substantially along the rim 18.

As shown in FIG. 2C, the screw retaining members 51, 52 are integrally formed with the cup portion 10 such that each screw retaining member 51, 52 is fixedly inclined relative to the rim 18. The inclination orientation is shown with reference to line or plane "I" in FIG. 2C. As indicated in FIG. 2C, inclination enables screws 100 to be located as close as possible to the outer surface 14 of the cup portion 10, an orientation that maximizes use of drillable bone in a dysplasic hip. Additionally, as further shown in FIG. 2B, the screw retaining members 51, 52 are also fixedly offset relative to the rim 18. The offset orientation is shown with reference to line or plane "O1" and "O2" in FIG. 2B. As shown in FIGS. 2B and 2C, the screw retaining members 51, 52 are oriented in a cooperative relationship with one another to facilitate implantation of the prosthesis 1 in one side of the hip of the patient.

In a preferred embodiment, each screw retaining member 51, 52 is inclined at an angle of between about 10 and about 25 degrees relative to the rim 18 (see FIG. 2C). In a most preferred embodiment, each screw retaining member 51, 52 is fixedly inclined at an angle of about 20 degrees relative to the rim 18. In a preferred embodiment, each screw retaining member 51, 52 is offset at an angle of between about 10 and about 25 degrees relative to the rim 18 (see FIG. 28). In a most, preferred embodiment, each screw retaining member 51, 52 is fixedly offset at an angle of about 20 degrees relative to the rim 18.

As shown in FIGS. 2B, 2C and 2D, each screw retaining member 51, 52 has a threaded hole 55, 56 therethrough. Each threaded hole 55, 56 is fixedly inclined relative to the rim 18 such that an axis of the threaded hole $T_1$) converges toward the axis (A) of the cup portion in one dimension (see FIG. 2C), and such that the axis of the threaded hole ($T_O1: T_O2$) is oblique to the axis (A) of the cup portion in a second dimension (see FIG. 2B).

Figure 2E:
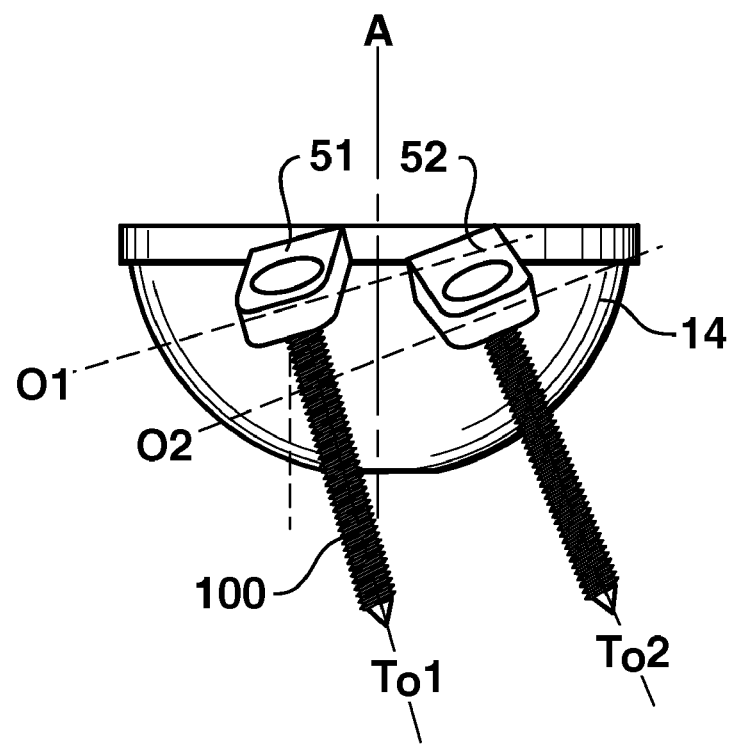
FIG. 2E is a side view of one preferred embodiment of the acetabular cup prosthesis of the invention showing screw retaining members that are slightly divergent from one another in the offset orientation, such that the screws have a toed-out or oblique relationship to one another.
Figure 2F:
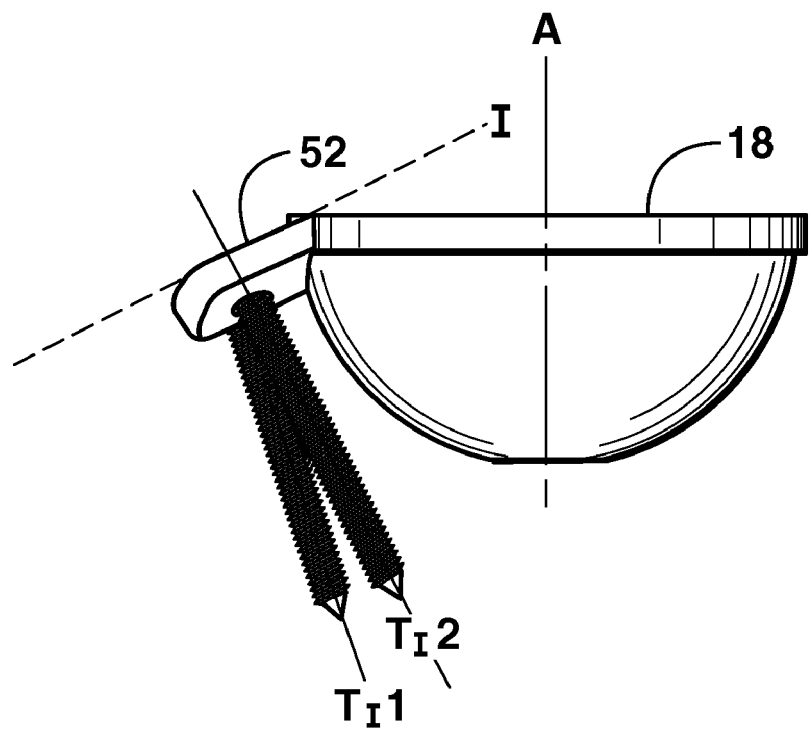
FIG. 2F is a side view of the cup of FIG. 2E rotated approximately 90 degrees from FIG. 2E to show screws in a toed-out or oblique relationship to one another.

As indicated in FIGS. 2, 3 and 4, the screw retaining members 51, 52 are adjacent to one another in order to maximize anchorage in the area of drillable bone. The screw retaining members 51, 52 preferably extend along an arc of between about 30 to about 60 degrees along the circumference of the rim 18. If two sets of screw retaining members 51, 52, 61, 62 are provided (discussed in further detail below), the screw retaining members 51, 52, 61, 62 preferably occupy an arc of less than about 90 degrees along the circumference of the rim 18, and preferably of about 75 degrees. As also indicated in FIG. 2B, the screw retaining members 51, 52 are preferably spaced apart a selected distance, such as about 10 mm (or an arc of between about 15 to 25 degrees, depending on the size of the prothesis). Spacing of the screw holes 55, 56 provides greater stability to the cup 1 when the prosthesis is implanted in an acetabulum. However, in situations where only a very small area of drillable bone is available, it may be preferable to have the screw retaining members 51, 52 directly adjacent to one another. For added strength, the first and second screw retaining members 51, 52 may he joined to one another, such as in the manner shown in FIG. 3, As shown in FIG. 2B, to provide cooperative fixation between the screw retaining members 51, 52, the screw retaining members may be oriented in a generally parallel relationship with one another (compare line/plane O1 with line/plane O2). Likewise, as also shown in FIG. 2B, the threaded holes 55, 56 of the pair of screw retaining members 51, 52 may be in a parallel relationship with one another (compare thread/fixation axes $T_O1$ and $T_O2$). A substantially parallel orientation of the threaded holes 55, 56 enables fixation about two generally parallel fixation axes in the patient's acetabulum. In some deficient hip conditions, a parallel orientation may contribute to maximal use of available bone, along with greater resistance to the forces encountered in the hip. However, in many applications it may be desireable to orient the screws 100 in a divergent or oblique orientation in relation to each other as shown in FIGS. 2E or 2F. A divergent orientation contributes greater pull-out strength to the screws and greater stability to rotational moments encountered in the hip joint. The divergent orientation includes toe-out and toe-in (technically, convergent) orientations. As shown most clearly in FIG. 2E, a divergent orientation can be accomplished by orienting the screw retaining members in an oblique relationship to one another, either in the offset, dimension, in the inclination dimension or, preferably, in both offset and inclination dimensions. In some cases, the divergent orientation will be generally, but not precisely, parallel.

As indicated in FIG. 2C, the axis of the threaded hole 55, 56 of the retaining members 51, 52 is preferably substantially perpendicular to the inclination of the screw retaining member 51, 52 (compare inclination thread/fixation axes $T_1$ with inclination line/plane I). As further indicated in FIG. 2B, the axis of the threaded hole 55, 56 of the retaining members 51, 52 is also preferably substantially perpendicular to the offset of the screw retaining member 51, 52.

One disadvantage of the embodiment shown in FIG. 2 is that the prosthesis can only be used in one side of a patient's hip, due to the cooperative inclination and offset orientations of the screw receiving members 51, 52. It is an object of the invention to reduce inventory by providing a cup prosthesis 1 that can be used in either a right or left acetabulum of a patient. This objective can be achieved, by providing a second set of screw retaining members 61, 62, such as in the embodiment, shown in FIG. 4A (see also FIG. 3). The second set of screw retaining members 61, 62 includes the orientations and characteristics described above with regard to the first set of screw retaining members 51, 52. However, as shown in FIG. 4B, the second set of screw retaining members 61, 62 is fixed in a substantially opposite or mirrored orientation in relation to the first set. of screw retaining members 51, 52. In the embodiment shown in FIG. 4B, the first set of screw retaining members 51, 52 are directly adjacent to one another, while the second set of screw retaining members 61, 62 are directly adjacent one another. In the embodiment shown in FIG. 4C, the first and second sets of screw retaining members are in a staggered relationship in which the screw retaining members of the first set 51, 52 alternate with screw retaining members of the second set 61, 62. One advantage of the staggered embodiment shown in FIG. 4C is that it allows the cooperative screw retaining members of each set to be spaced apart from one another, yet occupy a minimal arc along the rim 18. Note that in each case, the first pair of screw retaining members 51, 52 are oriented in a cooperative relationship with one another to facilitate implantation of the prosthesis in one side of the hip of a patient, while the second pair of screw retaining members 61, 62 are oriented in a cooperative relationship with one another to facilitate implantation of the prosthesis 1 in the opposing hip of the patient, in this manner, required inventory is reduced.

FIG. 3 shows a preferred embodiment of a unitary acetabular cup that can be used in either a right or left deficient acetabulum of a patient. As shown most clearly in FIGS. 3A and 3C, a flange 40 extends from the outer surface 14 of the dome 10 substantially along a portion of the rim 18. The flange 40 is integrally formed with the cup portion 10. As shown in FIG. 3C, the flange 40 is inclined relative to the rim 18. The flange is preferably inclined at between about 10 to 25 degrees relative to the rim 18. In the preferred embodiment shown in FIG. 3, the flange 40 is inclined at about 20 degrees relative to the rim 18.

Figure 3A:
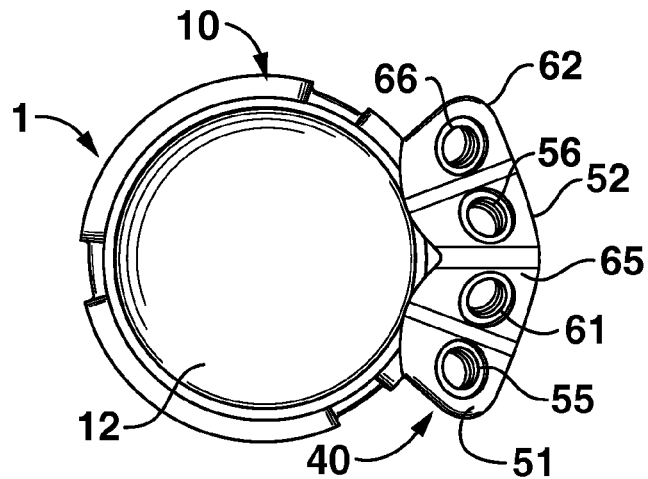
FIG. 3A is a top view of one preferred embodiment of the acetabular cup prosthesis of the invention configured for use in either a left or a right hip of a patient.

As shown in FIG. 3A, the flange 40 includes a first 51, 52 and a second 61, 62 pair of screw retaining members formed thereon for use in attaching the prosthesis to the patient's hip bone. The screw retaining members 51, 52, 61, 62 include the orientations and characteristics described above with reference to FIG. 2, except that the screw retaining members 51, 52, 61, 62 are oriented on a single flange 40. For example, as shown most clearly in FIG. 3B, each screw retaining member 51, 52, 61, 62 is fixedly inclined relative to the rim 18 and also fixedly offset relative to the rim 18. As shown in FIG. 3A, each screw retaining member has a threaded hole 55, 56, 65, 66 therethrough. As indicated in FIG. 3C, each threaded hole 55, 56, 65, 66 is fixedly inclined relative to the rim 18 such that an axis of the threaded hole converges toward the axis of the cup portion 10 in one dimension, in the manner described above with reference to FIG. 2C. Likewise, as indicated in FIG. 3B, the axis of each threaded hole is oblique to the axis of the cup portion in a second dimension (see thread lines/axes T1, T2, T3, T4), in the manner described above with reference to FIG. 2B.

Figure 3B:
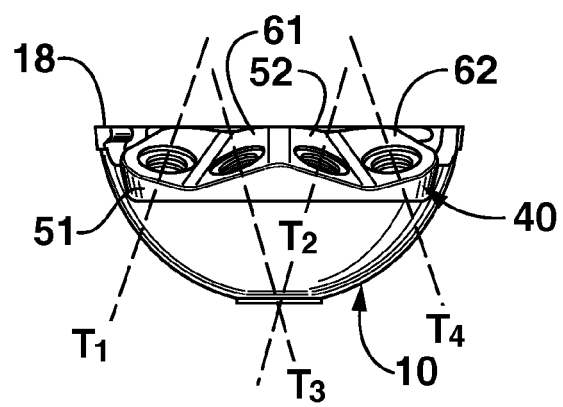
FIG. 3B is a side view down the flange portion of FIG. 3A, featuring orientation of two sets of screw retaining members on the flange, and indicating offset orientation of the threaded bores.
Figure 3C:
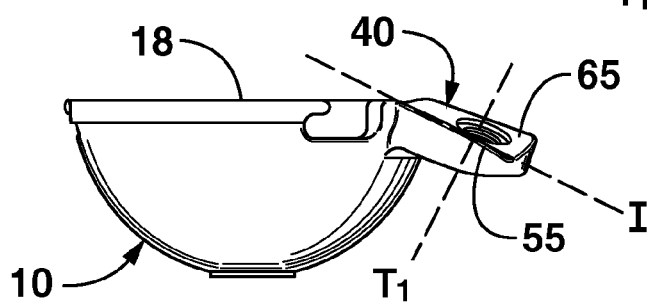
FIG. 3C is a side view of the cup of FIG. 3B, rotated approximately 90 degrees from FIG. 3B to show inclination the flange and an inclined orientation of the threaded bores.

As shown in FIG. 3B, the first pair of screw retaining members 51, 52 are fixed in a substantially parallel relationship with one another, and the second pair of screw retaining members 61, 62 are also fixed in a substantially parallel relationship with one another. As shown in FIG. 3B, the first 51,52 and second 61, 62 sets of screw retaining members are also fixed in an oblique relationship to one another, such that the prosthesis can be used on either a left or right acetabulum, in the manner described above. Ti the embodiment shown in FIG. 3, the first 51, 52 and the second 61, 62 pair of screw retaining members arranged in a staggered relationship, a configuration that minimizes the degree of arc required by the flange 40.

As indicated in FIG. 3B, the threaded holes 55, 56 of the first pair of screw retaining members 51, 52 are preferably in a substantially parallel relationship with one another (compare thread line/axes T1 and T2). Likewise, the threaded holes 65, 66 of the second pair of screw retaining members 61, 62 are in a substantially parallel relationship with one another (compare thread lines/axes T3 and T4). As shown in FIG. 3B, the threaded holes 55, 56 of the first pair of screw retaining members 51, 52 are in an oblique relationship with the threaded holes 65, 66 of the second pair of screw retaining members 61, 62, an orientation that enables the prosthesis 1 to be used on either a left or a right, acetabulum of the patient.

As further indicated in FIG. 3C, the axis T1 of the threaded hole 55 of each screw retaining member 51 is preferably substantially perpendicular to the inclination 1 of the screw retaining member 51. As indicated in FIG. 3B, the axis of the threaded hole 55 of each screw retaining member 51 is also preferably substantially perpendicular to the offset of the screw retaining member 51 (compare thread lines/axes T1, T2, T3 and T4 with the lower face of the corresponding screw retaining member).

Figure 7A:
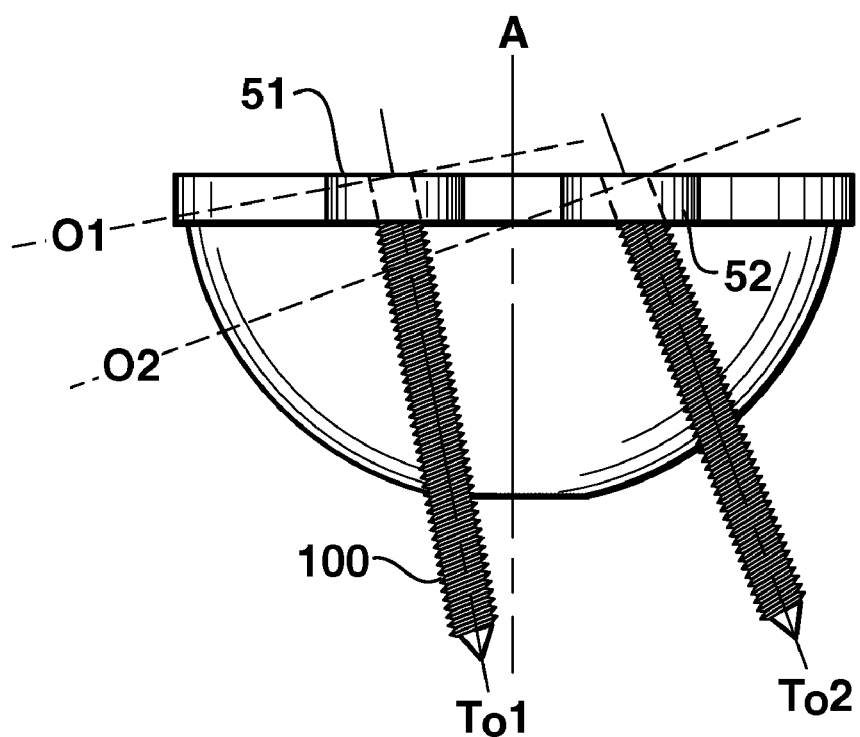
FIG. 7A is a side view of an alternative embodiment of the invention in which an offset orientation is provided by angulation of threaded bores alone.
Figure 7B:
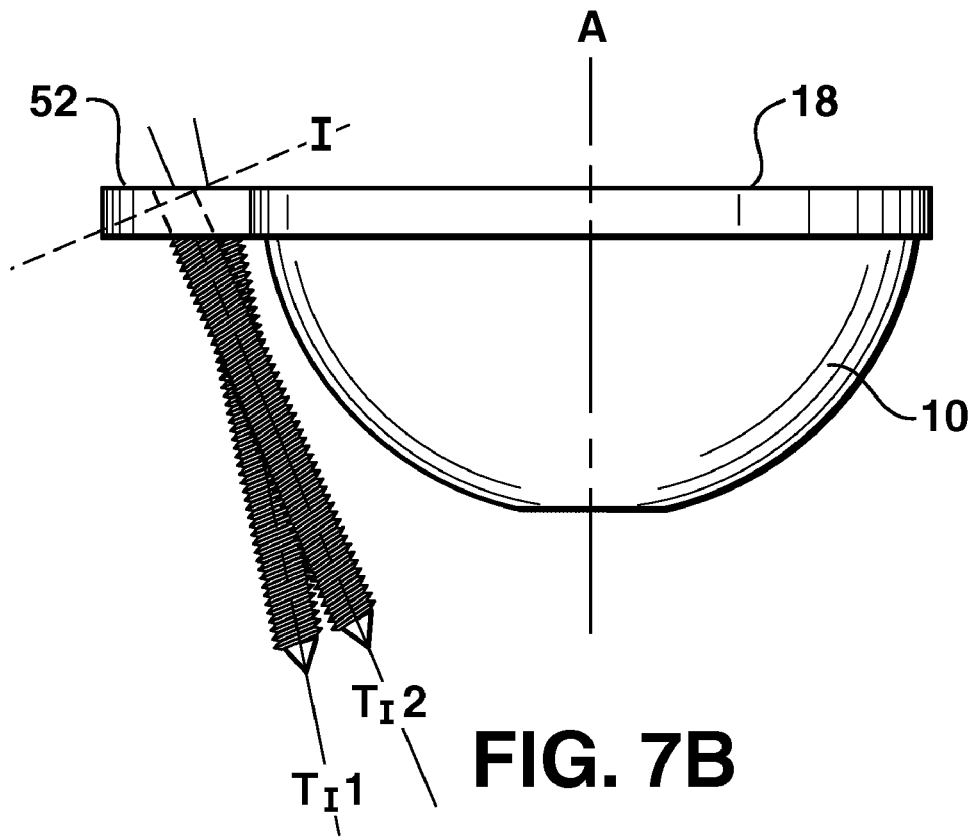
FIG. 7B is a side view of the cup of FIG. 2E rotated approximately 90 degrees from FIG. 7A to show an inclined orientation provided by angulation of threaded bores alone.

FIGS. 7A and 7B show an alternative embodiment in which inclination and offset are provided through inclination and offset of the threaded bores alone, rather than by inclination and offset of the screw retaining portions 51, 52. As shown in FIG. 7B, the embodiment employs squarely oriented screw retaining members 52 that extend substantially in the plane of the rim 18, i.e. substantially perpendicular to the axis A of the cup 10. As indicated in FIGS. 7A and 7B, the various offset and inclination angles discussed above can be obtained with this embodiment. However, the screw retaining member 51, 52 must project further laterally in order to obtain desired degrees of inclination. The squarely oriented retaining members 51, 52 could be provided on a single flange. A pair of squarely oriented retaining members 51, 52, 61, 62 could also be provided on a single flange 40 (not shown). It is also possible to provide offset retaining members having inclined bore holes or inclined retaining members having offset bore holes. Further, the inclined and offset angles of screws discussed above can be provided by using selected combinations of square, inclined, or offset retaining members and applicably oriented thread bores.

Figure 1B:
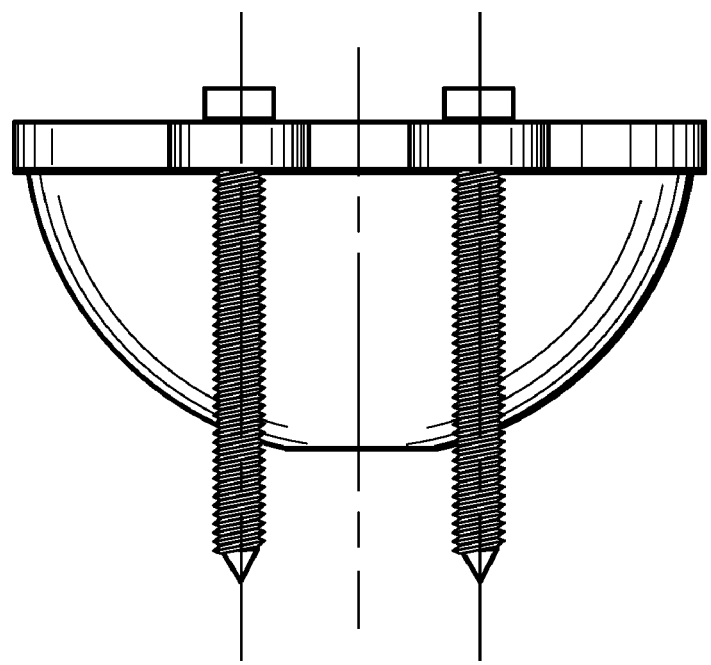
FIG. 1B is a side view of the prior art dysplasia cup of FIG. 1, rotated 90 degrees to the show the orientation of a pair of screws in screw retainer portions, the screws being parallel to the axis of the cup.
Figure 5A:
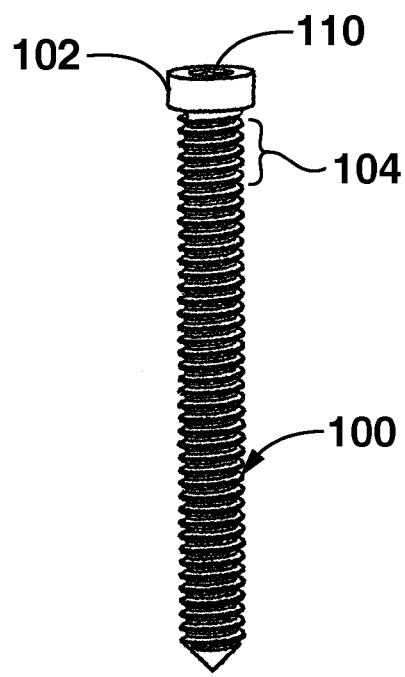
FIG. 5 provides views of preferred embodiments threaded screws for use with the acetabular cup prosthesis of the invention.
Figure 5B:
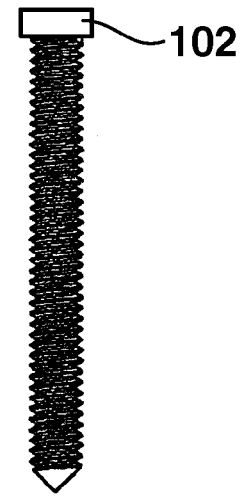
Figure 5C:
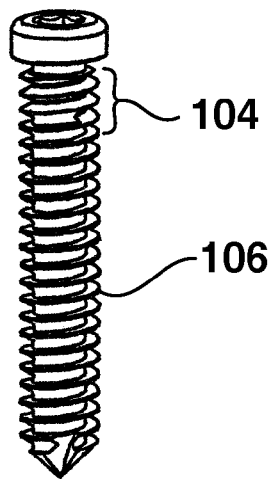
Figure 5D:
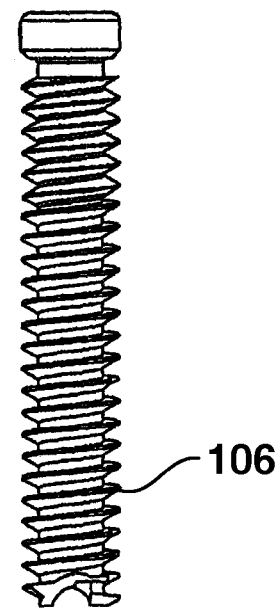

The prior art dysplasia cup shown in FIG. 1 employs screws having machine threads having a generally uniform pitch. FIGS. 5A-5B show a screw 100 for use in the invention that includes a machine thread as well as a head 102 configured to be countersunk in the screw retaining members 51, 52. To improve screw performance, the screws 100 are preferably provided with a bone screw thread 106, such as a cancellous bone thread, along a distal portion of the screw shaft for optimal threading in bone, and a machine thread along a proximal portion of the shaft 104 adjacent the screw head 102 for optimal threading in the threaded bore (FIGS. 5C-5D). The bone thread 106 preferably has a distal pitch of 30 degrees and a proximal pitch of 3 degrees. The thread in the proximal portion 104 of the shaft closely matches the thread of the screw bore in order to provide a locking fit and prevent the screw 100 from backing out of the threaded holes. The bone thread 106 is preferably blended with the machine thread 104 such that the bone thread 106 threads through the threaded bore during threading of the screw 100 into the bore of the cup 1. By "blended thread," applicant means that the machine 104 and bone 106 threads blend to form a single thread; the single thread, could, however, be discontinuous or interrupted along part of its length, such as to provide a self-drilling or tapping feature. To further enhance locking between the screw 100 and the threaded bore, a locking means such as double lead threads or mismatched threads may be used.

One disadvantage of the cups 1 shown in FIG. 3 is that the flange member 40 is relatively wide relative to the circumference of the rim 18, particularly in small sized cups. The size of the flange 40 can be reduced by using three rather than four holes. As discussed above, the prior art three-hole cups suffer from a number of drawbacks. The foregoing problems can be overcome with the alternative embodiment of a unitary acetabular cup prosthesis 1 shown in FIGS. 8A-8G. The prosthesis of FIG. 8 includes a cup portion 1 comprising a generally dome-shaped wall .10 having an axis and a substantially planar upper rim 18. An inner bearing surface 12 of the wall 10 is configured to pivotally engage a femoral head of a hip prosthesis.

Figure 8E:
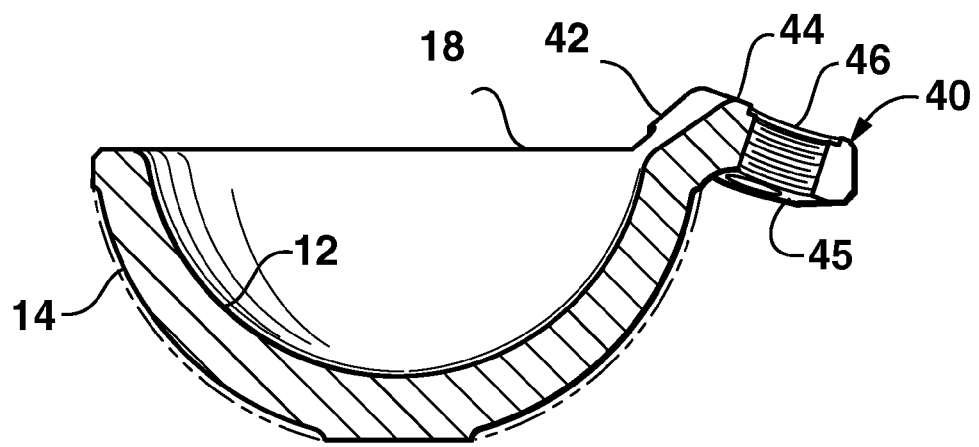
Figure 8F:
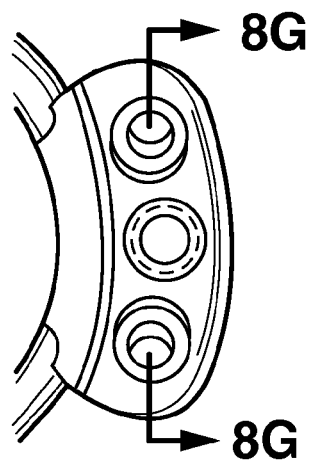

As shown in FIG. 8A, a flange member 40 is integrally formed with the cup portion 1. As shown perhaps most clearly in FIG. 8E, the flange member 40 has a base portion 42 that extends upward along a portion of the upper rim 18. The base portion 42 serves to raise a portion of the flange member 40 above the rim 18, which increases the conformity of the implant 1 to the acetabulum of the patient. A generally planar screw retaining portion 44 extends from the base portion 42. As shown in FIG. 8E, the screw retaining portion 44 is inclined from the base portion 42 such that at least a lateral portion of a lower surface 45 of the screw retaining portion 44 is positioned below the upper rim 18 while an upper surface 46 of the screw retaining portion 44 is positioned above the upper rim 18.

As shown in FIG. 8B, the screw retaining portion 44 has a first threaded hole 55, a second threaded hole 65 and a neutral threaded hole 56 formed therethrough. The neutral threaded hole 57 is positioned between the first and the second threaded holes 51, 61. As indicated in FIG. 8A, the first threaded hole 55, the neutral threaded hole 57, and the second threaded hole 65 are fixedly inclined relative to the rim 18 such that the axes $T_1$ of the threaded holes 55 incline toward the axis of the cup 1 portion in a first dimension viewed generally along a width-wise side of the flange member 40. As indicated in FIG. 8D, the axes of the first and second threaded hole 55, 65 are also offset laterally from the axis A of the cup portion 1 in a second dimension viewed generally along a length-wise side of the flange member 40. However, as indicated in FIG. 8D, the axis of the neutral threaded hole 57 is substantially parallel to the axis of the cup portion 1 in the second dimension. Because of this orientation, the neutral threaded hole 57 can be used with either the first or the second threaded hole 55, 65. The first, second and neutral threaded holes 55, 57, 65 are spaced sufficiently adjacent one another to allow the cup prosthesis 1 to be used in either a left or a right hip of a patient.

In a preferred embodiment, the screw retaining portion 44 of the flange member 40 is fixedly inclined at an angle of between about 15 and about 25 degrees relative to the upper rim 18, and most preferably at an angle of about 20 degrees relative to the upper rim 18. As indicated in FIG. 8A, the axis of each of the threaded hole 55, 57, 65 is preferably substantially perpendicular to the inclination of the flange member 40 in the first dimension. As further indicated in FIG. 8A, the axes of the first, the second and the neutral threaded holes 55, 57, 65 are substantially parallel to one another in the first dimension. The axes of each of the first and the second threaded holes 55, 65 preferably diverge from the axis of the neutral threaded hole 57 at an angle of between about 15 and about 25 degrees in the second dimension, and most preferably at an angle of about 20 degrees in the second dimension. As indicated in FIG. 8B, the first, the second and the neutral threaded holes 55, 57, 65 are preferably arranged radially along the screw retaining portion 44 of the flange member 40 substantially equidistant from the axis of the cup portion 1. As indicated in FIG. 8B, the flange member 40 preferably extends along an arc of less than about 60 degrees of the upper rim 18 of the cup 1. The first and the second 55, 65 threaded holes are preferably radially spaced about 20 degrees from the neutral threaded hole 57.

Figure 8G:
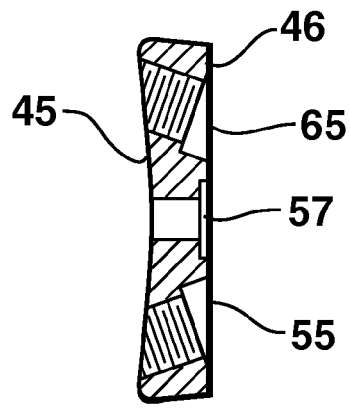

As shown in FIG. 8E, the upper surface 46 of the screw retaining portion 44 of the flange member 40 is preferably flat, A flat upper surface 46 facilitates manufacture of the prosthesis as well as the use of instrumentation during implantation of the cup 1. As shown in FIG. 8G, the lower surface 45 of the screw retaining portion 44 of the flange member 40 has a curved contour. In a preferred embodiment, the curved contour of the lower surface 45 is a conic section. The curved contour facilitates manufacture of the prosthesis and the use of instrumentation, and also increases the conformity of the prosthesis to bone.

The cup of FIG. 8 is universal in the sense that it can be used in either a left or right hip, which reduces inventory, such as in a surgical kit. When implanting the cup 1 of FIG. 8, the neutral threaded hole 57 and the anteriorly oriented first or second threaded holes 55, 65 will be used to secure the cup 1 in the acetabulum of the patient. The posteriorly oriented first or second, hole 55, 65 will typically not be used. Thus, when implanting in a right hip, the neutral hole 57 and the first threaded hole 55 will be used. When implanting in a left hip, the neutral hole 57 and the second threaded hole 65 will be used.

The implant 1 is preferably provided with additional features to assist in implantation of the prosthesis 1 into the acetabulum of the patient. As shown in FIG. 8B, the flange member 40 can be provided with an impactor space 26 for accommodating a portion of an impactor instrument, such that the upper rim 18 of the body of the cup 10 extends into and fills the impactor space. As shown in FIGS. 8A and 8B, the body of the cup 1 can also be provided with a plurality of impactor notches 20 formed through the rim 18 and the outer surface 14 of the dome 10, with each impactor notch having an associated impactor tab 22. The impactor notches 20 and associated impactor tabs 22 configured for selective engagement of the prosthesis by an impactor instrument.

The threaded holes 55, 57, 65 can be provided with a shallow counterbore for receiving and aligning a drill guide 200. The threaded holes 55, 57, 65 can also be configured to allow the head 102 of the retaining screws 100 to be at least partially countersunk in the screw retaining members 51, 52.

Figure 9A:
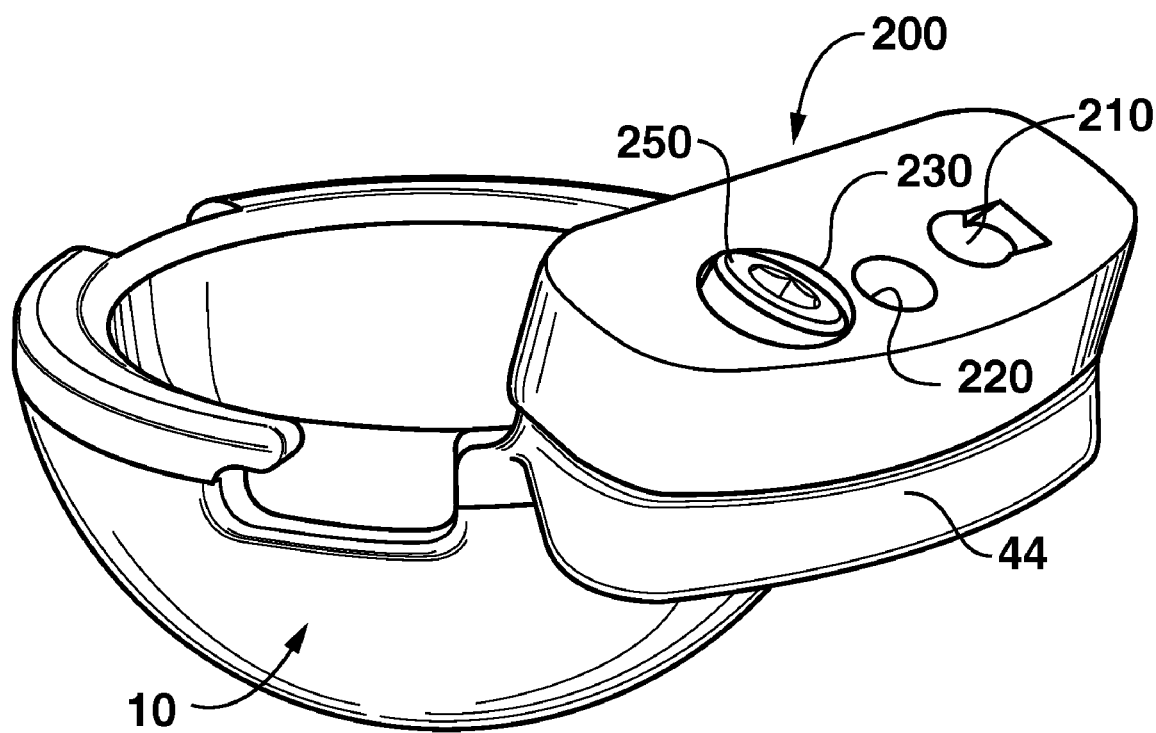
Figure 10A:
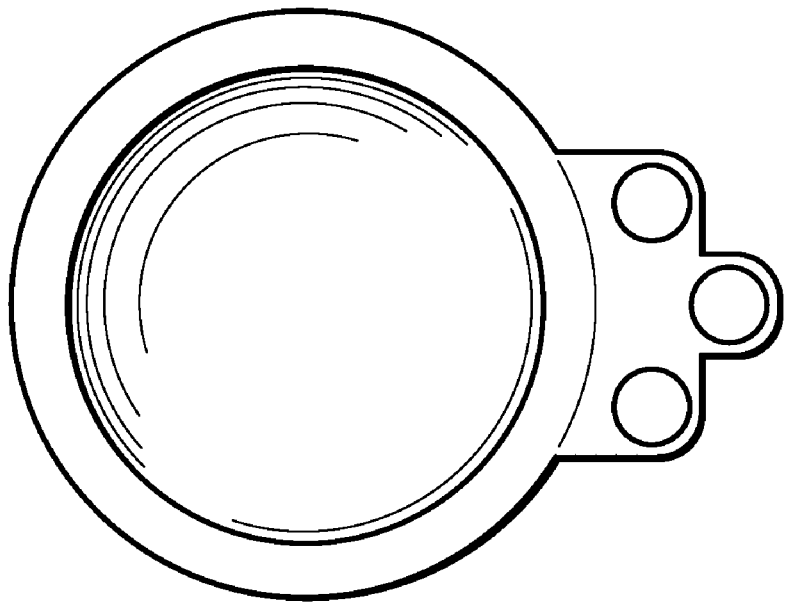
FIG. 10A-10B shows a prior art three-hole cup.
Figure 10B:
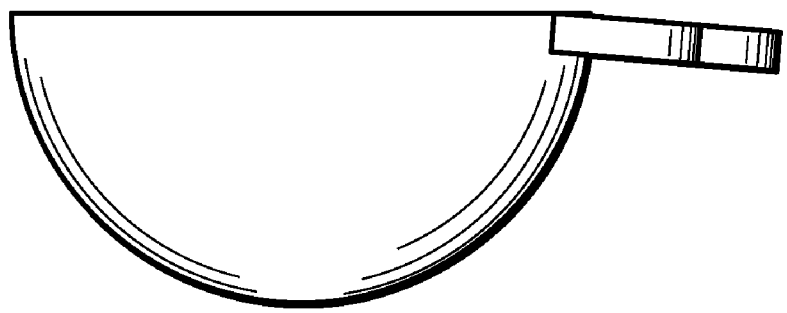

To further assist in implantation of the cup 1, a drill guide 200 of the type shown in FIGS. 9A-9E can be provided. The drill guide 200 is configured for use in drilling screw holes in the patient's acetabum, such that the screw holes are axially aligned with the threaded holes of the screw retaining portion 44 of the flange member 40 of the cup 1. As shown in FIG. 9B, the drill guide 200 comprises a plate 201 configured to overlay the upper surface 46 of the screw retaining portion 44 of the flange member 40. The plate 201 has a lateral drill guide bore 210 axially aligned with the first and the second threaded holes of the screw retaining portion 44, a neutral drill guide bore 220 axially aligned with the neutral threaded hole 57 of the screw retaining portion 44, and a set screw bore 230 axially aligned with the first and the second threaded holes of the screw retaining portion 44. As shown in FIG. 9A, when the drill guide 200 is selectively secured to the upper surface 46 of the screw retaining portion 44 by a set screw 250 positioned, in the lateral set screw bore 230 and threaded into either the first or the second threaded hole 55, 65, the lateral drill guide bore 210 and the neutral drill guide bore 220 are positioned for use in drilling screw holes through the threaded holes of the screw retaining member 44 and into the hip of the patient.

When the cup 1 is anteverted in the hip, the divergent orientation of the bores of the first and second threaded holes will make it difficult or perhaps impossible to use the posteriorly oriented first or second threaded hole 55, 65. However, the drill guide 200 has the added benefit of blocking the posterior threaded hole with the set screw 250, and therefore discouraging use of the posteriorly oriented threaded hole.

As shown in FIGS. 9B-9E, the drill guide 200 is preferably provided with features for use in aligning the drill guide 200 on the flange member 40. As shown in FIG. 9C, a lateral drill guide bore seat 212 extends below the lateral drill guide bore 210 for use in aligning the lateral drill guide bore 210 with either the first or the second threaded hole 55, 65. A neutral drill guide bore seat 222 extends below the neutral drill guide bore 220 for use in aligning the neutral drill guide bore 220 with the neutral threaded hole 57. A set screw bore seat 232 extends below the set screw bore 230 for use in aligning the set screw bore 230 with either the first or the second threaded hole 55, 65. In the preferred embodiment shown in FIGS. 9B-9D, the lateral drill guide bore seat 212 is substantially semi-circular, the neutral drill guide bore seat 222 is annular, and the set screw bore seat 232 is substantially semi-circular.

The implant can be provided in a kit format, such as a surgical kit. In a preferred embodiment, the kit includes a set of differently sized implants such as those shown in FIG. 8 and a drill guide of the type shown in FIG. 9. In another preferred embodiment, the kit includes a set of differently sized implants and a set of screws having blended threads such as the type shown in FIG. 5C. The components of the kit are preferably arranged in a convenient format, such as in a surgical tray or case. However, the kit components do not have to be packaged or delivered together. provided that they are assembled or collected together in the operating room for use at the time of surgery.

The prosthesis 1 is preferably made of a titanium alloy or a cobalt chromium, although various known materials may be suitable. Optionally, the outer surface 14 of the cup portion 10 has a controlled-porosity surface to enable bone growth to the prosthesis 1. The outer surface 14 may also be associated with a biologically active agent that enhances bone growth (e.g. bone-morphogenetic protein; growth factors; hydroxyapatite) to encourage bone growth to the prosthesis 1.

Various advantages arise from the configuration of the acetabular cup prosthesis 1, some of which are discussed above. The unique configuration of the acetabular cup prosthesis 1 enables it to be used as both a primary or a revision implant. The prosthesis provides for metal-on-metal articulation, resulting in minimal debris versus metal-on-UHMWPE prostheses. The invention 1 provides a rigid construct in which the angle of the screws is maintained, thus enabling the screws to maintain the cup 10 in position. The thin phalange 40 provides sufficient strength without impinging on implantation of the device.

Figure 3D:
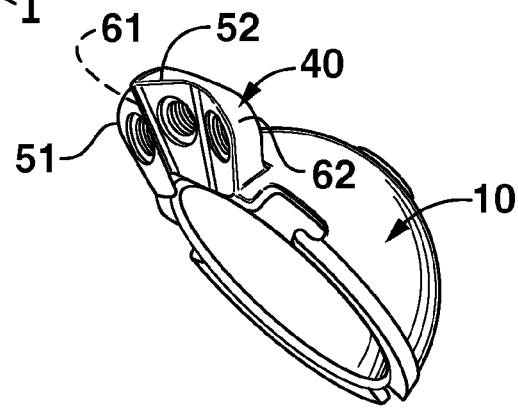
FIG. 3D is a perspective view of the cup of FIGS. 3A-3H, with the cup angled to indicate a preferred orientation of the cup in a right hip of a patient when viewed from the front of the patient along the median sagittal plane.
Figure 3E:
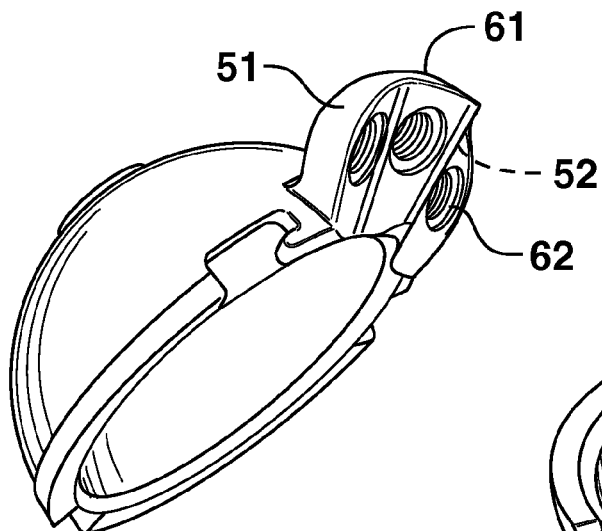
FIG. 3E is a perspective view of the cup of FIGS. 3A-3H, with the cup angled to indicate a preferred orientation of the cup in a left hip of a patient when viewed from the front of the patient along the median sagittal plane.
Figure 3F:
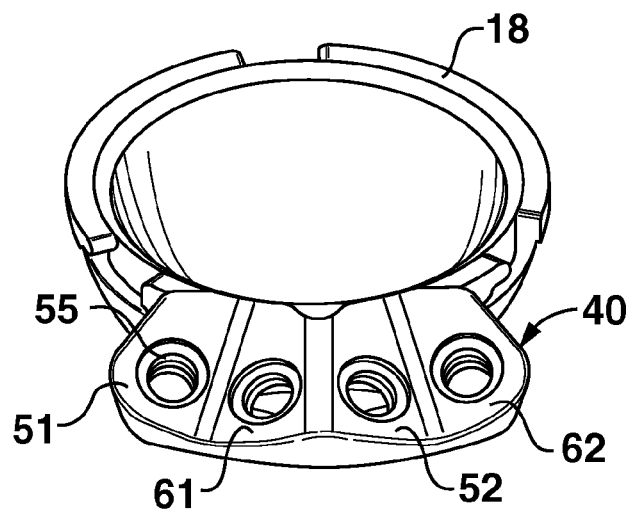
FIG. 3F is a perspective view of the preferred embodiment of FIGS. 3A-3H, rotated approximately 45 degrees forward from FIG. 3B.
Figure 3G:
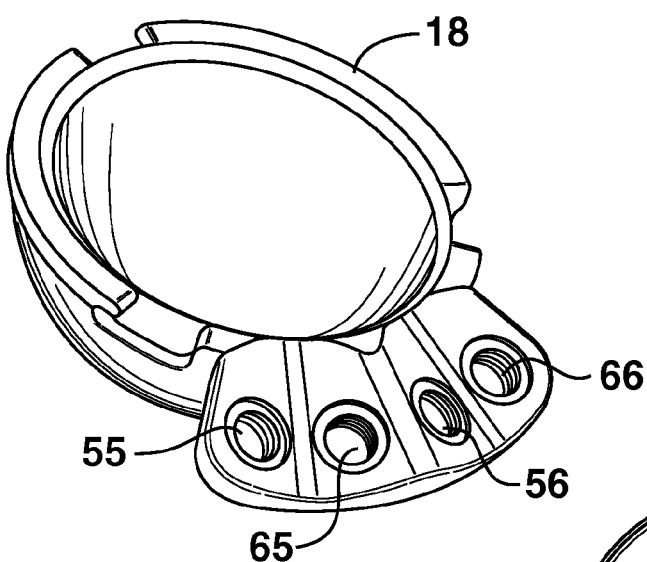
FIG. 3G is a further perspective view of the preferred embodiment of FIGS. 3A-H
Figure 3H:
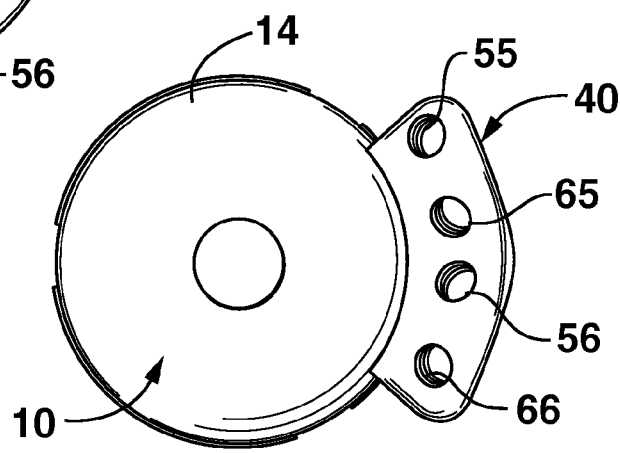
FIG. 3H is a bottom view of the preferred embodiment of FIGS. 3A-3H.
Figure 6A:
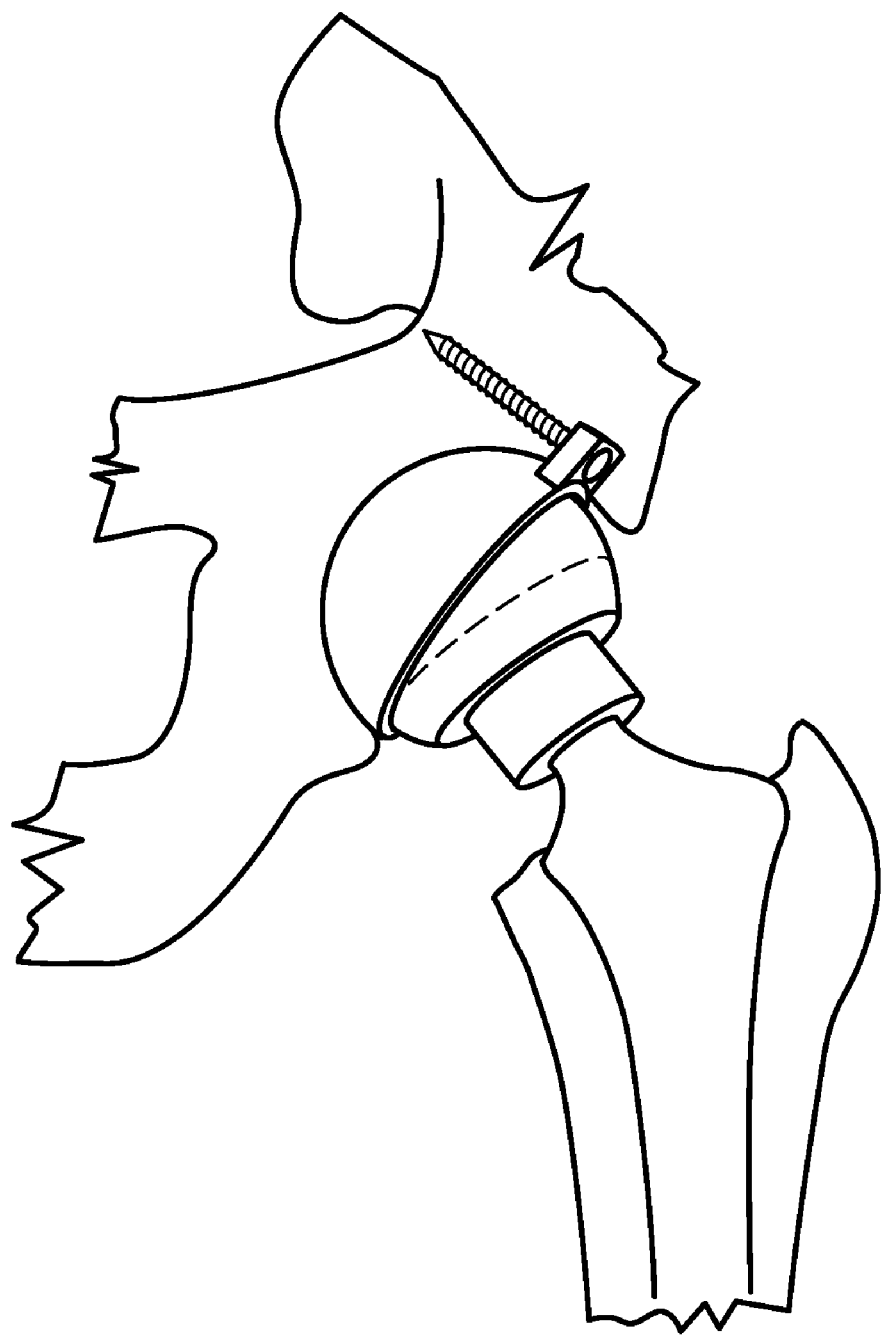
FIG. 6A is an x-ray view of the prior art dysplasia cup of FIG. 1 installed in a dysplasic hip of a patient, and indicating undesirable retroversion of the cup along the fiat contour of the dysplasic hip.
Figure 6B:
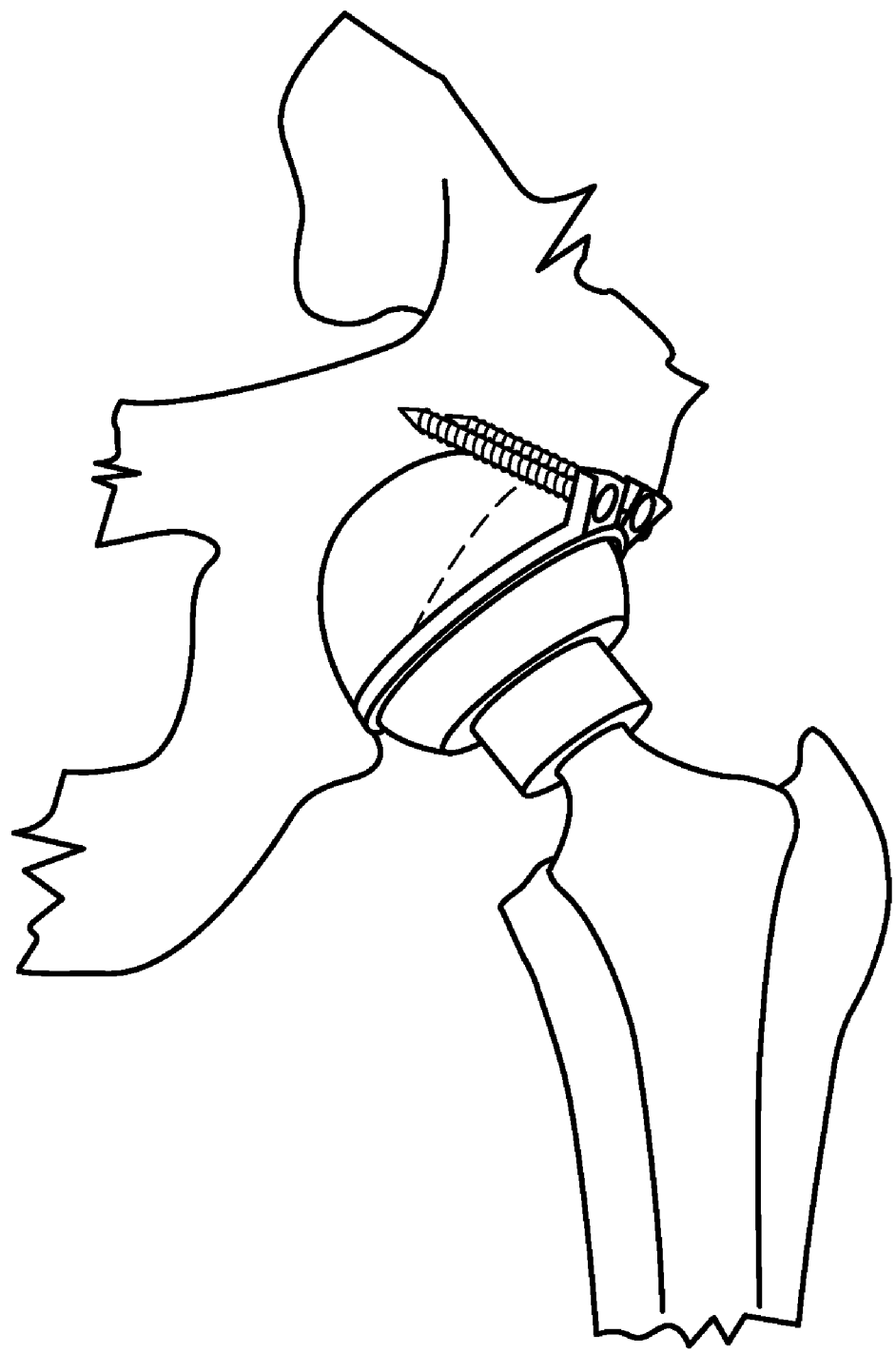
FIG. 6B is an x-ray view of one preferred embodiment of the acetabular cup prosthesis of the Invention installed in a deficient hip of a patient, indicating a preferred degree of anteversion of the cup versus prior art dysplasia cups such as the prior art cup shown in FIG. 6A.

Although the invention has been described as a unitary cup embodiment, the internal wall 12 of the cup 10 may alternatively be configured to receive an insert configured to articulate with the femoral head of femoral hip prosthesis, such as an UHMWPE or ceramic insert In operation, the acetabular cup prosthesis 1 is installed in a patient in much the same manner as a conventional cup or dysplasia cup. However, because of the unique angulation of the threaded bores, the cup 1 of the invention can be installed in a greater degree of anteverslon or retroversion compared to conventional dysplasia cups, such as the type shown in FIG. 1. As mentioned above, the flat contour and generally thinner cross-section of a dyplasic hip provides minimal hone for reaming or screwing, which makes it difficult to orient a cup in a sufficiently anteverted position. FIG. 6A provides an x-ray view of the prior art dysplasia cup of FIG. 1 installed in a dysplasic hip of a patient. Because of the location of the screws, the prior art cup must often be implanted in a somewhat retroverted position in order obtain a firm setting in available drillable bone, which can contribute to a dislocation. A phantom line along the femoral prosthesis head in FIG. 6A indicates a preferred position of the rim of the cup relative to the hip and the femoral prosthesis. FIG. 6B is an x-ray view of one preferred embodiment of the acetabular cup prosthesis 1 of the invention installed in a deficient hip of a patient. In FIG. 6B, the cup 1 is fixed in an orientation that is substantially identical to the desired position of a prosthesis in a non-dysplasic hip, and which thus minimizes the risk of dislocation. The phantom line in FIG. 6B indicates a typical position of the rim of prior art dyplasic cups in a dysplasic hip. FIG. 3D is a perspective view of the cup of FIGS. 3A-3H, with the cup angled to indicate a preferred orientation of the cup in a right hip of a patient when viewed from the front of the patient along the median sagittal plane. FIG. 3E is a perspective view of the cup of FIGS. 3A-3H, with the cup angled to indicate a preferred orientation of the cup in a left, hip of a patient when viewed from the front of the patient along the median sagittal plane. While exact orientations will vary from patient to patient, the prosthesis of the invention 1 will preferably be installed such that the rim 18 of the cup 1 is fixed at about 45 degrees relative to vertical and about 15 to 20 degrees anteversion, generally in the orientations shown in FIGS. 3D and 3E.

In order to minimize stability problems, a drill guide is preferably used to drill holes and insert the screws into the hip.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A unitary acetabular cup prosthesis for use in a deficient acetabulum of a hip bone of a patient, the prosthesis comprising:
    a cup portion comprising a generally dome-shaped wall having an axis and a substantially planar upper rim, an inner bearing surface of said wall configured to pivotally engage a femoral head of a hip prosthesis,
    a flange member integrally formed with said cup portion, said flange member comprising
        a base portion extending upward along a portion of said upper rim,
        a generally planar screw retaining portion, said screw retaining portion inclined from said base portion such that at least a lateral portion of a lower surface of said screw retaining portion is positioned below said upper rim while an upper surface of said screw retaining portion is positioned above said upper rim,
        said screw retaining portion having a first threaded hole, a second threaded hole and a neutral threaded hole formed therethrough, said neutral threaded hole positioned between said first and said second threaded holes,
        said first threaded hole fixedly inclined relative to said upper rim such that an axis of said first threaded hole inclines toward said axis of said cup portion in a first dimension viewed generally along a width-wise side of said flange member, and such that said axis of said first threaded hole is offset laterally from said axis of said cup portion in a second dimension viewed generally along a length-wise side of said flange member,
        said second threaded hole fixedly inclined relative to said upper rim such that an axis of said second threaded hole inclines toward said axis of said cup portion in said first dimension, and such that said axis of said second threaded hole is offset laterally from said axis of said cup portion and divergently from said axis of said first threaded hole in said second dimension,
        said neutral hole fixedly inclined relative to said upper rim such that an axis of said neutral threaded hole inclines toward said axis of said cup portion in said first dimension and such that said axis of said neutral threaded hole is substantially parallel to said axis of said cup portion in said second dimension, and
        said first, second and neutral threaded holes spaced sufficiently adjacent one another to thereby allow the prosthesis to be used in either a left or a right hip of a patient.

2. The prosthesis of claim 1, wherein said screw retaining portion of said flange member is fixedly inclined at an angle of between about 15 and about 25 degrees relative to said upper rim.

3. The prosthesis of claim 2, wherein said screw retaining portion of said flange member is fixedly inclined at an angle of about 20 degrees relative to said upper rim.

4. The prosthesis of claim 1, wherein said axis of each said threaded hole is substantially perpendicular to said inclination of said flange member in said first dimension.

5. The prosthesis of claim 1, wherein said axes of said first, said second and said neutral threaded holes are substantially parallel in said first dimension.

6. The prosthesis of claim 1, wherein said axes of each of said first and said second threaded holes diverge from said axis of said neutral threaded hole at an angle of between about 15 and about 25 degrees in said second dimension.

7. The prosthesis of claim 6, wherein said axes of each of said first and said second threaded holes diverge from said axis of said neutral threaded hole at an angle of about 20 degrees in said second dimension.

8. The prosthesis of claim 1, wherein said first, said second and said neutral threaded holes are arranged radially along said screw retaining portion of said flange member substantially equidistant from said axis of said cup portion.

9. The prosthesis of claim 1, wherein said flange member extends along an arc of less than about 60 degrees of said upper rim of said cup portion.

10. The prosthesis of claim 1, wherein said first and said second threaded holes are radially spaced about 20 degrees from said neutral threaded hole.

11. The prosthesis of claim 1, wherein said upper surface of said screw retaining portion of said flange member is flat to thereby facilitate manufacture of the prosthesis and use of instrumentation.

12. The prosthesis of claim 1, wherein said lower surface of said screw retaining portion of said flange member has a curved contour to thereby facilitate manufacture of the prosthesis and use of instrumentation and to increase conformity of the prosthesis to bone.

13. The prosthesis of claim 12, wherein said curved contour is a conic section.

14. The prosthesis of claim 1, further comprising said flange member having an impactor space for accommodating an impactor instrument, said upper rim extending into and filling said impactor space.

15. The prosthesis of claim 14, further comprising said cup portion having a plurality of impactor notches formed through said upper rim and said outer surface of said wall of said cup portion, each said impactor notch having an associated impactor tab, said impactor notches and associated impactor tabs configured for selective engagement of the prosthesis by an impactor instrument.

16. The prosthesis of claim 1, wherein said threaded holes are provided with a shallow counterbore for receiving and aligning a drill guide.

17. A unitary acetabular cup prosthesis for use in a deficient acetabulum of a hip bone of a patient, the prosthesis comprising:
 a prosthesis according to claim 1, and
 a pair of retaining screws, each said retaining screw having a head portion and a lengthwise screw shaft extending therefrom, said screw shaft having a blended thread,
 wherein a proximal portion of said blended thread is a machine thread portion configured to closely match an internal thread of said threaded holes to thereby prevent said screw from backing out of said threaded hole, and
 a distal portion of said blended thread is a bone thread portion configured to thread through said internal thread of said threaded hole and to also securely engage the hip bone of the patient.

18. The prosthesis of claim 17, wherein said machine thread portion of said blended thread extends along less than about one-fourth of said screw shaft, while said bone thread extends between said machine thread portion and a distal tip of said screw shaft.

19. The prosthesis of claim 17, wherein said bone thread portion preferably has a distal pitch of about 30 degrees and a proximal pitch of about 3 degrees.

20. The prosthesis of claim 17, wherein said first, said second and said neutral threaded holes are configured to allow said head of said retaining screws to be at least partially countersunk in said screw retaining members.

21. A kit combination for use in implanting a hip prosthesis in a deficient acetabulum of a patient comprising,
 a prosthesis according to claim 1,
 a drill guide for use in drilling screw holes axially aligned with said threaded holes of said screw retaining portion of said flange member of said prosthesis, said drill guide comprising a plate configured to overlay said upper surface of said screw retaining portion of said flange member, said plate having a lateral drill guide bore axially aligned with said first and said second threaded holes of said screw retaining portion, a neutral drill guide bore axially aligned with said neutral threaded hole of said screw retaining portion, and a set screw bore axially aligned with said first and said second threaded holes of said screw retaining portion, such that when said drill guide is selectively secured to said upper surface of said screw retaining portion by a set screw positioned in said lateral set screw bore and threaded into either said first or said second threaded hole, said lateral drill guide bore and said neutral drill guide bore are positioned for use in drilling screw holes through said threaded holes of said screw retaining member and into the hip of the patient.

22. The kit combination of claim 21, further comprising
 a lateral drill guide bore seat extending below said lateral drill guide bore for use in aligning said lateral drill guide bore with either said first or said second threaded hole,
 a neutral drill guide bore seat extending below said neutral drill guide bore for use in aligning said neutral drill guide bore with said neutral threaded hole, and
 a set screw bore seat extending below said set screw bore for use in aligning said set screw bore with either said first or said second threaded hole.

23. The kit combination of claim 21, wherein
 said lateral drill guide bore seat is substantially semi-circular, said neutral drill guide bore seat is annular, and said set screw bore seat is substantially semi-circular.

* * * * *